US010710952B2

(12) United States Patent
Shaver et al.

(10) Patent No.: US 10,710,952 B2
(45) Date of Patent: *Jul. 14, 2020

(54) PROCESS FOR FLASHING A REACTION MEDIUM

(71) Applicant: CELANESE INTERNATIONAL CORPORATION, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/130,428

(22) Filed: Sep. 13, 2018

(65) Prior Publication Data

US 2019/0010109 A1 Jan. 10, 2019

Related U.S. Application Data

(63) Continuation of application No. 15/089,994, filed on Apr. 4, 2016, now Pat. No. 10,099,990, which is a continuation of application No. 14/789,006, filed on Jul. 1, 2015, now Pat. No. 9,302,975.

(51) Int. Cl.
*C07C 51/12* (2006.01)
*C07C 51/44* (2006.01)
*C07C 41/01* (2006.01)
*B01J 31/20* (2006.01)
*B01J 31/26* (2006.01)
*B01J 27/20* (2006.01)
*B01D 3/00* (2006.01)

(52) U.S. Cl.
CPC .............. *C07C 51/12* (2013.01); *B01D 3/009* (2013.01); *B01J 27/20* (2013.01); *B01J 31/20* (2013.01); *B01J 31/26* (2013.01); *C07C 41/01* (2013.01); *C07C 51/44* (2013.01); *B01J 2231/34* (2013.01)

(58) Field of Classification Search
CPC .................................. C07C 51/44; C07C 51/12
See application file for complete search history.

(56) References Cited

U.S. PATENT DOCUMENTS

| 3,769,329 | A | 10/1973 | Paulik et al. |
| 3,791,935 | A | 2/1974 | Eubanks et al. |
| 4,008,131 | A | 2/1977 | Price |
| 4,615,806 | A | 10/1986 | Hilton |
| 5,001,259 | A | 3/1991 | Smith et al. |
| 5,026,908 | A | 6/1991 | Smith et al. |
| 5,144,068 | A | 9/1992 | Smith et al. |
| 5,416,237 | A | 5/1995 | Aubigne et al. |
| 5,625,095 | A | 4/1997 | Miura et al. |
| 5,653,853 | A | 8/1997 | Kagotani et al. |
| 5,696,284 | A | 12/1997 | Baker et al. |
| 5,731,252 | A | 3/1998 | Warner et al. |
| 5,783,731 | A | 7/1998 | Fisher et al. |
| 5,877,347 | A | 3/1999 | Ditzel et al. |
| 5,877,348 | A | 3/1999 | Ditzel et al. |
| 5,883,295 | A | 3/1999 | Sunley et al. |
| 5,932,764 | A | 8/1999 | Morris et al. |
| 5,942,460 | A | 8/1999 | Garland et al. |
| 6,066,762 | A | 5/2000 | Yoneda et al. |
| 6,143,930 | A | 11/2000 | Singh et al. |
| 6,225,498 | B1 | 5/2001 | Blay et al. |
| 6,339,171 | B1 | 1/2002 | Singh et al. |
| 6,458,996 | B1 | 10/2002 | Muskett |
| 6,657,078 | B2 | 12/2003 | Scates et al. |
| 6,677,480 | B2 | 1/2004 | Huckman et al. |
| 7,005,541 | B2 | 2/2006 | Cheung et al. |
| 7,223,883 | B2 | 5/2007 | Picard et al. |
| 7,223,886 | B2 | 5/2007 | Scates et al. |
| 7,820,855 | B2 | 10/2010 | Patt |

(Continued)

FOREIGN PATENT DOCUMENTS

| JP | H0867650 A | 3/1996 |
| JP | H10231267 A | 9/1998 |

(Continued)

OTHER PUBLICATIONS

Zhu, Y. et al. (Apr. 2009). "Techno-economic Analysis for the Thermochemical Conversion of Lignocellulosic Biomass to Ethanol via Acetic Acid Synthesis," prepared for U.S. Department of Energy, PNNL-18483, Pacific Northwest National Laboratory, Richland, WA, 79 pages.

International Search Report received in the corresponding International Application No. PCT/US2015/053783, dated Mar. 4, 2016. (11 pgs.).

Celanese Chemicals, Product Description, "Acetic Acid, Glacial (Ethanoic Acid, Methanecarboxylic Acid)", Acetic Acid, Chemical Abstracts Registry, No. 67-19-7, 2000.

Celanese, "Acetic Acid", Celanse—The chemistry inside innovationTM, 2013. Brochure.

Title—"Control of propionic acid content in acetic acid production by carbonylation of methanol", Aug. 25, 2013, 20, pp. 50-52, p. 51, right column, line 4-13.

Title—"Control of formation of ethanol in methanol", Sep. 15, 2007, 5th period, pp. 21-22, left column, lines 8-16.

(Continued)

*Primary Examiner* — Paul A Zucker

(74) *Attorney, Agent, or Firm* — Kilpatrick Townsend & Stockton LLP

(57) ABSTRACT

A process for producing acetic acid is disclosed in which the methyl iodide concentration is maintained in the vapor product stream formed in a flashing step. The methyl iodide concentration in the vapor product stream ranges from 24 to less than 36 wt. % methyl iodide, based on the weight of the vapor product stream. In addition, the acetaldehyde concentration is maintained within the range from 0.005 to 1 wt. % in the vapor product stream. The vapor product stream is distilled in a first column to obtain an acetic acid product stream comprising acetic acid and up to 300 wppm hydrogen iodide and/or from 0.1 to 6 wt. % methyl iodide and an overhead stream comprising methyl iodide, water and methyl acetate.

9 Claims, 1 Drawing Sheet

(56) References Cited

U.S. PATENT DOCUMENTS

| | | |
|---|---|---|
| 7,855,306 B2 | 12/2010 | Zinobile et al. |
| 7,884,237 B2 | 2/2011 | Shaver |
| 7,884,241 B2 | 2/2011 | Miura et al. |
| 8,062,482 B2 | 11/2011 | Warner |
| 8,173,076 B2 | 5/2012 | Powell et al. |
| 8,318,977 B2 | 11/2012 | Zinobile et al. |
| 8,697,908 B2 | 4/2014 | Torrence et al. |
| 8,889,904 B2 | 11/2014 | Shaver et al. |
| 9,006,483 B2 | 4/2015 | Shimizu et al. |
| 9,193,657 B2 | 11/2015 | Scates et al. |
| 9,302,975 B1 * | 4/2016 | Shaver .................... C07C 51/44 |
| 9,382,183 B1 | 7/2016 | Shaver et al. |
| 9,776,941 B2 | 10/2017 | Shimizu |
| 10,099,990 B2 * | 10/2018 | Shaver .................... C07C 51/44 |
| 2006/0011462 A1 | 1/2006 | Horiguchi et al. |
| 2008/0214866 A1* | 9/2008 | Miura .................... C07C 51/44 562/608 |
| 2012/0090981 A1 | 4/2012 | Torrence et al. |
| 2013/0116470 A1 | 5/2013 | Miura et al. |
| 2013/0261334 A1 | 10/2013 | Shimizu et al. |
| 2013/0264186 A1 | 10/2013 | Shimizu et al. |
| 2013/0281735 A1 | 10/2013 | Shimizu et al. |
| 2013/0303800 A1 | 11/2013 | Shimizu |
| 2013/0310603 A1 | 11/2013 | Shimizu et al. |
| 2017/0260120 A1 | 9/2017 | Shimizu et al. |
| 2017/0349521 A1 | 12/2017 | Shimizu et al. |

FOREIGN PATENT DOCUMENTS

| | | |
|---|---|---|
| JP | 4489487 B2 | 6/2010 |
| WO | 2014/115826 A1 | 7/2014 |

OTHER PUBLICATIONS

Title—"A method to reduce ethanol content in purified methanol", Aug. 25, 2010, vol. 33, No. 4, pp. 225-227, p. 225, left column, line 2-9.

Title—"Purification of crude methanol", Jan. 15, 1997, 1997, $1^{st}$ period, pp. 1-5 and 11, p. 2, left column, line 24-right column, line 3.

Kirk-Othmer Encyclopedia of Chemical Technology $4^{th}$ Ed, Mass Transfer to Neuroregulators, a Wiley-Interscience publication; John Wiley & Sons, Inc., vol. 16, 1995, p. 554, lines 9-17.

IMPCA Methanol Reference Specifications, International Methanol Producers & Consumers Association, Dec. 9, 2010, p. 1.

Title: "Specification of ethanol content of methanol products", May 15, 2008, 2008, $3^{rd}$ period, pp. 52-54, p. 53, left column, lines 14-20.

Title: "Consideration for four-column distillation process for methanol production", Sep. 20, 1998, 1998, $9^{th}$ period, pp. 21-22.

* cited by examiner

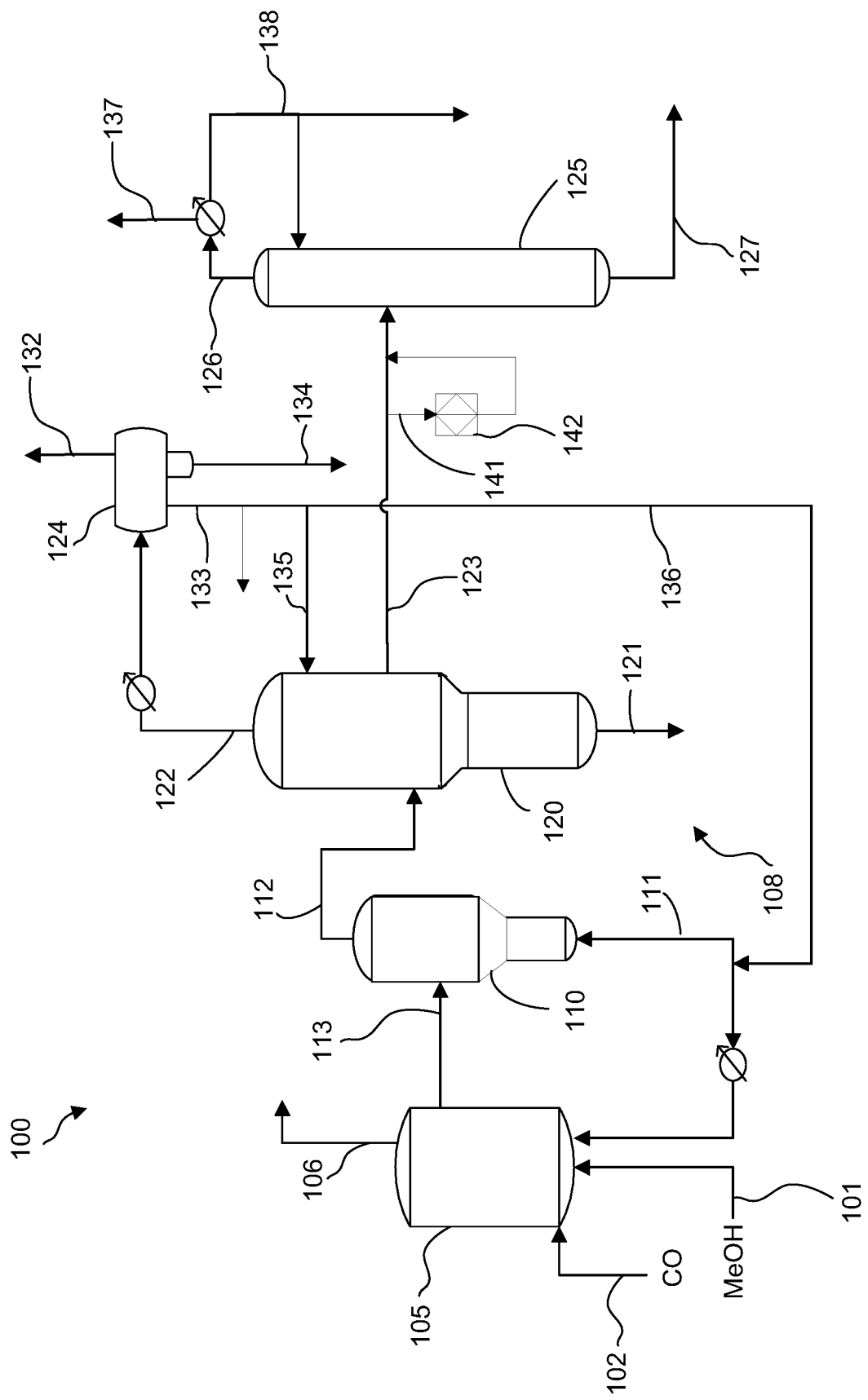

PROCESS FOR FLASHING A REACTION MEDIUM

This application is a continuation of U.S. application Ser. No. 15/089,994, filed on Apr. 4, 2016, which issued as U.S. Pat. No. 10,099,990, which is a continuation of U.S. application Ser. No. 14/789,006, filed on Jul. 1, 2015, which issued as U.S. Pat. No. 9,302,975, the entirety of which is incorporated herein by reference.

FIELD OF THE INVENTION

This invention relates to processes for producing acetic acid and, in particular, to improved processes for flashing a crude acetic acid product in an acetic acid production system.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, which is incorporated herein by reference in its entirety. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. The reaction is conducted by continuously bubbling carbon monoxide gas through a liquid reaction medium in which the catalyst is dissolved.

Methanol and carbon monoxide are fed to a reactor as feedstocks. A portion of the reaction medium is continuously withdrawn and provided to a flash vessel where the product is flashed and sent as a vapor to a purification train. The purification train includes a light ends column which removes "light" or low boiling components as an overhead and provides a sidedraw stream for further purification. The purification train may further include columns to dehydrate the sidedraw stream or for removing "heavy" or high boiling components, such as propionic acid, from the sidedraw stream. It is desirable in a carbonylation process for making acetic acid to minimize the number of distillation operations to minimize energy usage in the process.

U.S. Pat. No. 5,416,237 discloses a process for the production of acetic acid by carbonylation of methanol in the presence of a rhodium carbonylation catalyst, methyl iodide and an iodide salt stabilizer by maintaining a finite concentration of water of up to about 10% by weight and a methyl acetate concentration of at least 2% by weight in the liquid reaction medium and recovering the acetic acid product by passing the liquid reaction medium through a flash zone to produce a vapor fraction which is passed to a single distillation column from which an acetic acid product is removed. The vapor fraction comprises water up to about 8% by weight, acetic acid product, propionic acid by-product and the majority of the methyl acetate and methyl iodide.

U.S. Pat. No. 7,820,855 discloses a carbonylation process for producing acetic acid including: (a) carbonylating methanol or its reactive derivatives in the presence of a Group VIII metal catalyst and methyl iodide promoter to produce a liquid reaction mixture including acetic acid, water, methyl acetate and methyl iodide; (b) feeding the liquid reaction mixture at a feed temperature to a flash vessel which is maintained at a reduced pressure; (c) heating the flash vessel while concurrently flashing the reaction mixture to produce a crude product vapor stream, wherein the reaction mixture is selected and the flow rate of the reaction mixture fed to the flash vessel as well as the amount of heat supplied to the flash vessel is controlled such that the temperature of the crude product vapor stream is maintained at a temperature less than 90° F. cooler than the feed temperature of the liquid reaction mixture to the flash vessel and the concentration of acetic acid in the crude product vapor stream is greater than 70% by weight of the crude product vapor stream. Through the flash vessel the product acetic acid and the majority of the light ends (methyl iodide, methyl acetate, and water) are separated from the reactor catalyst solution, and the crude process stream is forwarded with dissolved gases to the distillation or purification section in single stage flash. The methyl iodide concentrations decrease as the temperature of the flash vessel is increased and the flow rates are decreased.

U.S. Pat. No. 9,006,483 discloses a production process of acetic acid that seeks to inhibit the concentration of hydrogen iodide and provide a liquid-liquid separation of an overhead from a distillation column. Acetic acid is produced by distilling a mixture containing hydrogen iodide, water, acetic acid and methyl acetate in a first distillation column to form an overhead and a side cut stream or bottom stream containing acetic acid, cooling and condensing the overhead in a condenser to form separated upper and lower phases in a decanter. According to this process, a zone having a high water concentration is formed in the distillation column above the feed position of the mixture by feeding a mixture having a water concentration of not less than an effective amount to not more than 5% by weight (e.g., 0.5 to 4.5% by weight) and a methyl acetate concentration of 0.5 to 9% by weight (e.g., 0.5 to 8% by weight) as the mixture to the distillation column and distilling the mixture. In the zone having a high water concentration, hydrogen iodide is allowed to react with methyl acetate to produce methyl iodide and acetic acid.

The need remains for improved acetic acid production processes having improved separation steps, increased production capacities and lower operating costs.

SUMMARY OF THE INVENTION

In one embodiment, the present invention is a process for producing acetic acid comprising withdrawing a reaction medium from a reactor; separating the reaction medium in a flash vessel into a liquid recycle stream and a vapor product stream comprising from 45 to 75 wt. % acetic acid, from 24 to less than 36 wt. % methyl iodide, up to 9 wt. % methyl acetate, up to 15 wt. % water, from 0.005 to 1 wt. % acetaldehyde, and up to 1 wt. % hydrogen iodide; and distilling at least a portion of the vapor product stream in a first column to obtain an acetic acid product stream comprising acetic acid and up to 300 wppm hydrogen iodide, preferably up to 50 wppm hydrogen iodide, and an overhead stream comprising methyl iodide, water and methyl acetate. In a preferred embodiment, the vapor product stream comprises from 55 to 75 wt. % acetic acid, from 24 to 35 wt. % methyl iodide, from 0.5 to 8 wt. % methyl acetate, from 0.5 to 14 wt. % water, from 0.01 to 0.8 wt. % acetaldehyde, and up to 0.5 wt. % hydrogen iodide. In another preferred embodiment, the vapor product stream comprises from 60 to 70 wt. % acetic acid, from 25 to 35 wt. % methyl iodide, from 0.5 to 6.5 wt. % methyl acetate, from 1 to 8 wt. % water, from 0.01 to 0.7 wt. % acetaldehyde, and up to 0.1 wt. % hydrogen iodide. In addition to low hydrogen iodide concentrations in the acetic acid product stream, the vapor product stream may also comprise from 0.1 to 6 wt. % methyl iodide and from 0.1 to 6 wt. % methyl acetate. The water concentration is maintained in the acetic acid product stream from 1 to 9 wt. %.

In one embodiment, the liquid recycle stream comprises from 0.01 to 0.5 wt. % metal catalyst; from 5 to 20 wt. % lithium iodide; from 10 to 2500 wppm corrosion metals; from 60 to 90 wt. % acetic acid; from 0.5 to 5 wt. % methyl iodide; from 0.1 to 5 wt. % methyl acetate; from 0.1 to 8 wt. % water; from 0.0001 to 1 wt. % acetaldehyde; and from 0.0001 to 0.5 wt. % hydrogen iodide.

The overhead stream from the first column, e.g., lights end column, may be phase separated to form a light liquid phase and a heavy liquid phase. The light liquid phase may comprise from 1 to 40 wt. % acetic acid, up to 10 wt. % methyl iodide, from 1 to 50 wt. % methyl acetate, from 40 to 80 wt. % water, up to 5 wt. % acetaldehyde, and up to 2 wt. % hydrogen iodide. More preferably, the light liquid phase may comprise from 15 to 25 wt. % acetic acid, from 1 to 5 wt. % methyl iodide, from 1 to 10 wt. % methyl acetate, from 60 to 75 wt. % water, from 0.1 to 0.7 wt. % acetaldehyde, and from 0.001 to 0.5 wt. % hydrogen iodide.

In another embodiment the present invention relates to a process for producing acetic acid comprising separating a reaction medium withdrawn from a reactor in a flash vessel into a liquid recycle stream and a vapor product stream comprising from 45 to 75 wt. % acetic acid, from 24 to less than 36 wt. % methyl iodide, up to 9 wt. % methyl acetate, up to 15 wt. % water, from 0.005 to 1 wt. % acetaldehyde, and up to 1 wt. % hydrogen iodide; and distilling at least a portion of the vapor product stream in a first column to obtain an acetic acid product stream comprising acetic acid and from 0.1 to 6 wt. % methyl iodide and an overhead stream comprising methyl iodide, water and methyl acetate.

In another embodiment the present invention relates to a process for producing acetic acid comprising distilling a mixture comprising from 45 to 75 wt. % acetic acid, from 24 to less than 36 wt. % methyl iodide, up to 9 wt. % methyl acetate, up to 15 wt. % water, and up to 1 wt. % hydrogen iodide to form an overhead stream comprising methyl iodide and sidedraw stream comprising acetic acid; and condensing the overhead stream to form separate liquid phases. The mixture may also comprise from 0.005 to 1 wt. % acetaldehyde. In one embodiment, the sidedraw stream has a water concentration that is maintained from 1 to 3 wt. %, and hydrogen iodide concentration that is maintained up to 300 wppm.

BRIEF DESCRIPTION OF THE DRAWING

The present invention will be better understood in view of the appended non-limiting figure, wherein:

FIG. is a schematic drawing for producing acetic acid in accordance with the present invention.

DETAILED DESCRIPTION OF THE INVENTION

Introduction

The production of acetic acid via the carbonylation of methanol involves the formation of a reaction medium in a reactor, and flashing the reaction medium in a flash vessel to form a liquid recycle stream and a vapor product stream. The vapor product stream is then distilled in one or more distillation columns to remove byproducts and form an acetic acid product. The present invention provides processes for making acetic acid while reducing byproduct formation by maintaining a specific methyl iodide concentration in the vapor product stream formed in the flash step. Methyl iodide is a useful promoter for the carbonylation catalyst. During separation, however, methyl iodide tends to concentrate with the acetic acid that is separated from the reaction medium and must be separated and returned to the reaction medium to avoid costly losses through fugitive emissions and to reduce iodide impurities in the acetic acid product. According to the present invention, methyl iodide concentrations are maintained at a sufficient level in the vapor product to support increased production rates while reducing the amount of methyl iodide that must be recovered from the vapor product stream. Reducing the amount of methyl iodide advantageously debottlenecks the distillation columns due to the lower amounts of methyl iodide that must be separated. Debottlenecking the distillation columns advantageously increases production capacities and lowers operating costs. In addition to increasing production capacity, maintaining methyl iodide at desired levels in the vapor product also beneficially affects the hydrogen iodide concentrations in the downstream distillation columns, with reduced hydrogen iodide levels resulting in reduced corrosion.

In one embodiment, the vapor product stream comprises from 24 to less than 36 wt. % methyl iodide based on the total weight of the vapor product stream, e.g., from 24 to 35 wt. % methyl iodide, or more preferably from 25 to 35 wt. % methyl iodide. As shown in U.S. Pat. No. 7,820,855, production rates decrease as methyl iodide concentrations decrease, based on mass flow rate from the reactor to the flash vessel. The present invention seeks to maintain higher production rates without the decrease in mass flow rate as described in U.S. Pat. No. 7,820,855.

Methyl iodide concentrations that are less than 24 wt. % results in undesirably reduced production rates. On the other hand, vapor product streams having methyl iodide concentrations of 36 wt. % or more increases the load on the distillation columns needed to remove methyl iodide, which impacts production capacity. Methyl iodide cannot be eliminated in the vapor product stream. Maintaining methyl iodide concentration in the range from 24 to less than 36 wt. % in the vapor product is important to control hydrogen iodide formation, which results from the hydrolysis of methyl iodide. Hydrogen iodide is a known corrosion-causing compound and may undesirably concentrate with methyl iodide concentrations above 36 wt. %. in the vapor product stream. Thus, having a vapor product stream with 24 wt. % to less than 36 wt. % methyl iodide may provide the desired hydrogen iodide control.

The vapor product may be sampled using on-line measuring techniques to measure methyl iodide content and provide real time or near real time feedback. Sampling the vapor product stream on-line is easier than sampling the liquid reaction medium. In addition, the concentration of the methyl iodide in the vapor product is related to and provides an indirect indication of the concentration of methyl iodide in the reactor. The ability to maintain a consistent methyl iodide concentration in the vapor product stream is useful to setting up a schedule for adding methyl iodide to the reactor. For example, in a commercial process, small amounts of methyl iodide are lost due to fugitive emissions and the use of various purge streams in the separation system. As the methyl iodide concentration in the vapor product decreases, additional methyl iodide may be added to the reactor. Conversely, when the methyl iodide concentration is too high, a portion of the heavy liquid phase from the light ends column may be purged from the system.

In addition to methyl iodide, the vapor product stream also comprises acetic acid, methyl acetate, and water. By-products such as hydrogen iodide, acetaldehyde, and propionic acid may also be present in the vapor product stream. The reactants, i.e., methanol and carbon monoxide, when not consumed, may be recovered in the vapor product stream. In one embodiment, the vapor product stream comprises from 45 to 75 wt. % acetic acid, from 24 to less than 36 wt. % methyl iodide, up to 9 wt. % methyl acetate, and up to 15 wt. % water, based on the total weight of the vapor product stream. More preferably, the vapor product stream comprises from 55 to 75 wt. % acetic acid, from 24 to 35 wt. % methyl iodide, from 0.5 to 8 wt. % methyl acetate, and from 0.5 to 14 wt. % water. In yet a further preferred embodiment, the vapor product stream comprises from 60 to 70 wt. % acetic acid, from 25 to 35 wt. % methyl iodide, from 0.5 to 6.5 wt. % methyl acetate, and from 1 to 8 wt. % water. The acetaldehyde concentration in the vapor product stream may be from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than 0.01 wt. %. In addition to acetaldehyde, there may also be other permanganate reducing compounds ("PRC's"), such as acetone, methyl ethyl ketone, butylaldehyde, crotonaldehyde, 2-ethyl crotonaldehyde, 2-ethyl butyraldehyde, and the aldol condensation products thereof. These compounds, if present in the vapor product stream, are generally in an amount similar to or less than the acetaldehyde concentrations. The vapor product stream may comprise hydrogen iodide in an amount up to 1 wt. %, based on the total weight of the vapor product stream, e.g., up to 0.5 wt. %, or up to 0.1 wt. %. The vapor product stream is preferably substantially free of, i.e., contains less than 0.0001 wt. %, propionic acid, based on the total weight of the vapor product stream.

The present invention also advantageously facilitates maintaining a water balance in the separation system and, in particular, during the distillation steps by controlling the net production of water. As a result, the invention beneficially inhibits or prevents increases in water content that may necessitate the purging of water from the system. Purging of water can also adversely result in the loss of catalyst promoters such as methyl iodide. In exemplary embodiments, the net production of water in the distilling step increases by less than 0.5% over the water concentration in the vapor product stream fed to the distilling step, e.g., by less than 0.1% or by less than 0.05%. In contrast, U.S. Pat. No. 9,006,483 describes promoting reactions that lead to the formation of water and allows for adding more water to the distilling step. Increases in the net production of water would be expected to be higher due to the promotion of these reactions and additions, leading to increased load on distillation equipment.

The vapor product stream is fed to a distillation column, e.g., a first column, which may also be referred to as a light ends column. In one optional embodiment, a portion of the vapor product stream may be condensed. The first column separates the vapor product stream to form an overhead stream, a product stream, and optionally a bottoms stream. The acetic acid product stream may be withdrawn as a sidedraw stream, and more preferably as a liquid sidedraw stream. In one embodiment, the acetic acid product stream primarily comprises acetic acid and may also comprise water, methyl iodide, methyl acetate, or hydrogen iodide. The acetic acid product stream withdrawn in the sidedraw preferably comprises more than 90 wt. % acetic acid, based on the total weight of the sidedraw stream, e.g., more than 94 wt. % or more than 96 wt. %. In terms of ranges, the acetic acid product stream comprises acetic acid in an amount from 90 to 99 wt. %, e.g., from 91 to 98 wt. %. Such concentrations allow a majority of the acetic acid fed to the first column to be withdrawn in the sidedraw stream for further purification. Although minor amounts of acetic acid may be present, acetic acid is preferably not recovered as a product in the overhead or bottoms of the first column.

The process preferably includes a step of maintaining a water concentration in the sidedraw stream in an amount from 1 to 9 wt. %, e.g., from 1 to 3 wt. %, and more preferably from 1.1 to 2.5 wt. %. The hydrogen iodide concentration in the sidedraw may be up to 300 wppm, e.g., up to 100 wppm, up to 50 wppm. In terms of ranges, the sidedraw stream preferably comprises hydrogen iodide in an amount from 0.05 to 300 wppm, based on the total weight of the sidedraw stream, e.g., from 0.1 to 50 wppm, or from 5 to 30 wppm. Hydrogen iodide is soluble in acetic acid-water mixtures containing water in an amount from 3 to 8 wt. %, and the solubility of hydrogen iodide decreases as the water concentration decreases. This correlation results in increasing hydrogen iodide volatility, which leads to reduced amounts of hydrogen iodide being collected in the overhead of the column. Although hydrogen iodide has been indicated by others to be corrosive, a certain amount of hydrogen iodide under some conditions may beneficially act as a catalyst, such as a catalyst for forming dimethyl ether as described in U.S. Pat. No. 7,223,883 (describing the benefits of dimethyl ether formation in certain acetic acid separation processes), the entirety of which is incorporated herein by reference.

The sidedraw stream may also comprise one or more $C_1$-$C_{14}$ alkyl iodides in an amount from 0.1 to 6 wt. %, and in particular methyl iodide, based on the total weight of the sidedraw stream. Other alkyl iodides such as hexyl iodide may also be formed from carbonyl impurities such as acetaldehyde. The sidedraw stream preferably comprises one or more $C_1$-$C_{14}$ alkyl iodides from 0.5 to 3 wt. %. Due to the presence of water, the sidedraw stream may also contain methyl acetate in a concentration from 0.1 to 6 wt. % based on the total weight of the sidedraw stream, e.g., from 0.5 to 3 wt. %.

Maintaining the desired methyl iodide concentration in the vapor product stream is an improvement over other processes that focus on water and methyl acetate concentrations in the vapor product that feeds the first column, such as those described in U.S. Pat. No. 9,006,483. Unlike water and methyl acetate, methyl iodide loss can represent a significant loss in terms of cost due to its significant value. The invention therefore allows for the recovery of valuable catalyst promoter, e.g., methyl iodide, which may be separated and returned to the reactor.

Hydrogen iodide concentration of the sidedraw stream is determined by potentiometric titration using lithium acetate as the titrant. Others have determined hydrogen iodide content indirectly by calculation. US Pub. No. 2013/0310603, for example, indicates that iodide ion concentration may be calculated by subtracting the iodide ion concentration derived from the iodide salt form (including iodides derived from co-catalysts and metal iodide) from the total concentration of iodide ion ($I^-$). Such indirect calculation techniques are typically inaccurate, resulting in a poor indication of actual hydrogen iodide concentration owing largely to the inaccuracies of the underlying ion measurement methods. In addition, this indirect calculation technique fails to account for other iodide forms because metal cations are measured and incorrectly assumed to be completely associated only with iodide anions while, in fact, the metal cations may be associated with other anions, such as acetate and catalyst anions. In contrast, the direct measurement of hydrogen iodide concentration according to the present invention advantageously reflects the actual hydrogen iodide concentration in the system, and can result in accuracy as low as 0.01%.

Reaction Step

An exemplary reaction and acetic acid recovery system 100 is shown in FIG. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to methyl acetate in the liquid reaction medium by esterification reaction with acetic acid.

Typical reaction temperatures for carbonylation will be from 150 to 250° C., with the temperature range of 180 to 225° C. being preferred. The carbon monoxide partial pressure in the reactor may vary widely but is typically from 2 to 30 atm, e.g., from 3 to 10 atm. The hydrogen partial pressure in the reactor is typically from 0.05 to 2 atm, e.g., from 0.25 to 1.9 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably about 15 to 35 mol/L·h.

Carbonylation reactor 105 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, which are incorporated herein by reference in their entireties. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entireties.

The halogen-containing catalyst promoter of the catalyst system may include an organic halide, such as an alkyl, aryl, and substituted alkyl or aryl halides. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide. In one embodiment, the methyl iodide concentration is maintained in the vapor product stream at a concentration from 24 wt. % to less than 36 wt. %. In one embodiment, the reaction medium may have methyl iodide concentration of 7 wt. % or less, e.g., from 4 to 7 wt. %.

The components of the reaction medium are maintained within defined limits to ensure sufficient production of acetic acid. The reaction medium contains a concentration of the metal catalyst, e.g. rhodium catalyst, in an amount from 200 to 3000 wppm, e.g., from 800 to 3000 wppm, or from 900 to 1500 wppm. The concentration of water in the reaction medium is maintained to be up to 15 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains 0.1 to 4.1 wt. % water, e.g., from 0.1 to 3.1 wt. % or from 0.5 to 2.8 wt. %. The concentration of methyl iodide in the reaction medium is maintained to be from 3 to 20 wt. %, e.g., from 4 to 13.9 wt. %, or from 4 to 7 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The concentration of acetic acid in the reaction medium is generally more than 30 wt. %, e.g. more than 40 wt. % or more than 50 wt. %.

In some embodiments, the desired reaction rates are obtained even at low water concentrations by maintaining an ester concentration in the reaction medium of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide (MeI) promoter, methyl acetate (MeAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide, the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, it is preferred that it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reaction system, which comprises the reactor and flash vessel. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof.

The reaction medium is drawn off from the carbonylation reactor 105 at a rate sufficient to maintain a constant level therein and is provided to flash vessel 110 via stream 113. Reactor 105 and flash vessel 110, along with the associated pumps, vents, pipes, and values, comprise the reaction system. The flash separation may be carried out at a temperature from 80° C. to 280° C., under an absolute pressure from 0.25 to 10 atm, and more preferably from 100° C. to 260° C. and from 0.3 to 10 atm. In one embodiment, the flash vessel may operate under a reduced pressure relative to the reactor. In flash vessel 110, the reaction medium is separated in a flash separation step to obtain a vapor product stream 112 comprising acetic acid and methyl iodide, as described herein, and liquid recycle stream 111 comprising a catalyst-containing solution.

Liquid recycle stream 111 comprises acetic acid, the metal catalyst, corrosion metals, as well as other various compounds. In one embodiment, liquid recycle stream comprises from 60 to 90 wt. % acetic acid, from 0.01 to 0.5 wt. % metal catalyst; from 10 to 2500 wppm corrosion metals (e.g., nickel, iron and chromium); from 5 to 20 wt. % lithium iodide; from 0.5 to 5 wt. % methyl iodide; from 0.1 to 5 wt. % methyl acetate; from 0.1 to 8 wt. % water; up to 1 wt. % acetaldehyde (e.g., from 0.0001 to 1 wt. % acetaldehyde); and up to 0.5 wt. % hydrogen iodide (e.g., from 0.0001 to 0.5 wt. % hydrogen iodide).

The respective flow rates of vapor product stream 112 and liquid recycle stream 111 may vary, and in one exemplary embodiment from 15% to 55% of the flow into flash vessel 110 is removed as vapor product stream 112, and from 45% to 85% of the flow is removed as liquid recycle stream 111. The catalyst-containing solution may be predominantly acetic acid containing the metal catalyst, e.g., rhodium and/or iridium, and the iodide salt along with lesser quantities of methyl acetate, methyl iodide, and water and is recycled to reactor 105, as discussed above. Prior to returning the liquid recycle stream to the reactor, a slip stream may pass through a corrosion metal removal bed, such as an ion exchange bed, to remove any entrained corrosion metals as described in U.S. Pat. No. 5,731,252, which is incorporated herein by reference in its entirety. Also, the corrosion metal removal bed may be used to remove nitrogen compounds, such as amines, as described in U.S. Pat. No. 8,697,908, which is incorporated herein by reference in its entirety.

In addition to acetic acid, methyl iodide and acetaldehyde, vapor product stream 112 also may comprise methyl acetate, water, hydrogen iodide, and other PRC's, e.g., crotonaldehyde. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 may be fed to the base of flash vessel 110 to enhance rhodium stability.

Recovery of Acetic Acid

The distillation and recovery of acetic acid is not particularly limited for the purposes of the present invention. As shown in FIG., vapor product stream 112 comprising from 24 to less than 36 wt. % methyl iodide is directed to a first column 120, also referred to as a light ends column. In one embodiment, vapor product stream 112 comprises acetic acid, methyl acetate, water, methyl iodide, and acetaldehyde, along with other impurities such as hydrogen iodide and/or crotonaldehyde, and/or byproducts such as propionic acid. Distillation yields a low boiling overhead vapor stream 122, a purified acetic acid product that preferably is removed via a sidedraw stream 123, and a high boiling residue stream 121. A majority of the acetic acid is removed in sidedraw stream 123 and preferably little or no acetic acid is recovered from high boiling residue stream 121.

In one embodiment, low boiling overhead vapor stream 122 comprises more than 5 wt. % water, e.g., more than 10 wt. % water, or more than 25 wt. % water, and optionally up to 80 wt. % water. In terms of ranges, the low boiling overhead vapor stream 112 may comprise water in an amount from 5 wt. % to 80 wt. %, e.g., from 10 wt. % to 70 wt. % or from 25 wt. % to 60 wt. %. Reducing the water concentration to less than 5 wt. % is generally not advantageous because it results in a large acetic acid recycle stream back to the reaction system, and increases the recycle stream throughout the entire purification system. In addition to water, low-boiling overhead vapor stream 122 may also comprise methyl acetate, methyl iodide, and carbonyl impurities, such as PRC's, which are preferably concentrated in the overhead vapor stream to be removed from acetic acid in sidedraw stream 123.

As shown, low boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, will biphasically separate into a light liquid phase 133, also referred to as an aqueous phase, and a heavy liquid phase 134, also referred to as an organic phase. An offgas component may be vented via line 132 from decanter 124. Although the specific compositions of light liquid phase 133 may vary widely, some preferred compositions are provided below in Table 1.

TABLE 1

Exemplary Phase Compositions from Light Ends Overhead

| (wt. %) | Light Liquid Phase | | Heavy Liquid Phase | |
|---|---|---|---|---|
| $H_2O$ | 40-80 | 60-75 | Up to 3 | 0.01 to 1 |
| MeAc | 1-50 | 1-10 | 1-20 | 5-15 |
| AcOH | 1-40 | 15-25 | 0.5-10 | 0.7-5 |
| PRC's (AcH) | Up to 5 | 0.1-0.7 | Up to 5 | 0.05-0.5 |
| MeI | Up to 10 | 1-5 | 60-95 | 80-90 |
| HI | Up to 1 | 0.001-0.5 | Up to 1 | 0.001-0.5 |

The concentration of components in sidedraw stream 123, such as water and/or hydrogen iodide, may be controlled by the recycle rate of light liquid phase 133 to the reaction system. The reflux ratio (the mass flow rate of the reflux divided by the total mass flow exiting the top of the column 120, including both heavy liquid phase 134, which may or may not be fully recycled, and light liquid phase 133) to the first column of the light liquid phase 133 via line 135 preferably is from 0.05 to 0.4, e.g., from 0.1 to 0.35 or from 0.15 to 0.3. In one embodiment, to reduce the reflux ratio, the number of theoretical trays above the sidedraw stream and top of first column may be greater than 5, e.g., preferably greater than 10. In one embodiment, a flow valve and/or flow monitor (not shown) may be used to control the reflux in line 135 and recycle in line 136.

In one embodiment, the recycle of light liquid phase in line 136 to the reaction system is up to about 20%, e.g., up to about 10%, of the total light liquid phase 133 condensed from the first column overhead. In terms of ranges the recycle of light liquid phase in line 136 may be from 0 to 20%, e.g., from 0.5 to 20% or from 1 to 10%, of the total light liquid phase 133 condensed from the first column overhead. The remaining portion may be used as a reflux on the light ends column or fed to an PRC removal system. For example, recycle in line 136 may be combined with liquid recycle stream 111 and be returned to reactor 105. In one embodiment, recycle in line 136 may be combined with another stream that is being recycled to the reaction system, e.g., reactor 105 or flash vessel 110. When condensed overhead stream 138 from drying column 125 is phase separated into an aqueous phase and an organic phase, the recycle in line 136 may be preferably combined with the aqueous phase. Alternatively, recycle in line 136 may be combined, or at least partially combined, with heavy liquid phase 134 and/or the organic phase from the overhead stream 138.

Carbonyl impurities, such as acetaldehyde, in the system may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the light liquid phase. Thus, a portion (preferably an aliquot portion) of light liquid phase 133 may be separated in stream 142 and directed to an acetaldehyde or PRC removal system 140 to recover methyl iodide and methyl acetate. As shown in Table 1, light liquid phase 133 contains PRC's, and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entireties.

In some embodiments, all or a portion of light liquid phase 133 and/or heavy liquid phase 134 may be directed to a PRC removal system as described above. Preferably the portion(s) directed to the PRC removal system as well as the reflux rate of light liquid phase 133 may be controlled so as to provide the desired balance of hydrogen iodide in sidedraw stream 123 and water recycle to the reactor.

In some embodiments, all or a portion of heavy liquid phase 134, which contains more methyl acetate and methyl iodide than light liquid phase 133, may also be recycled to reactor 105 and/or refluxed to first column 120. Additional carbonyl impurities may be removed from heavy liquid phase 134 using a similar process as described herein for light liquid phase 133.

In some embodiments, the process includes one or more on-line analyzers for measuring the concentrations of various components in the various streams. For example, an on-line analyzer may be used to determine the hydrogen iodide concentration of sidedraw stream 123 by feeding a sample stream, e.g., a sample purge stream, to an on-line analyzer (not shown).

Acetic acid removed via sidedraw stream 123 preferably is subjected to further purification, such as in a second column 125, also referred to as a drying column. The second column separates sidedraw stream 123 into an overhead stream 126 comprising primarily water, and bottoms stream 127 comprising primarily acetic acid. Acetic acid may also be recovered as a side stream near the bottom of second column 125. Overhead stream 126 optionally comprises from 50 to 75 wt. % water. Residual methyl acetate and methyl iodide are also removed from the sidedraw stream and concentrated in the overhead stream of the drying column. Drying column bottoms stream 127 preferably comprises or consists essentially of acetic acid. For purposes the present invention, bottoms stream 127 may be removed in the residue or column 125 or near the bottom of column 125. In preferred embodiments, drying column bottoms stream 127 comprises acetic acid in an amount greater than 90 wt. %, e.g., greater than 95 wt. % or greater than 98 wt. %. Drying column bottoms stream 127 may be further processed, e.g., by passing through an ion exchange resin, prior to being stored or transported for commercial use.

Similarly, overhead stream 126 from second column 125 contains a reaction component, such as methyl iodide, methyl acetate, and water, and it is preferable to retain these reaction components within the process. As shown, overhead stream 126 is condensed by a heat exchanger into stream 138, which is recycled to reactor 105 and/or refluxed second column 125. An offgas component may be vented via line 137 from condensed low-boiling overhead vapor stream 126. Similar to the condensed low-boiling overhead vapor stream from first column 120, condensed overhead stream 138 may also be separated into a light liquid phase and a heavy liquid phase. These phases may be recycled or refluxed as needed to maintain the desired component concentrations in the reaction medium.

To recover residual liquids from the vent stream, in particular lines 106, 132, and 137, these lines may be fed to a scrubber that operates with cooled methanol and/or acetic acid to remove methyl acetate and methyl iodide. A suitable scrubber is described in U.S. Pat. No. 8,318,977, which is incorporated herein by reference in its entirety.

The distillation columns of the present invention may be conventional distillation column, e.g., a plate column or a packed column, among others. The material used to form the distillation columns is not limited and may include glass, metal, ceramic, or any other suitable material. For a plate column, the number of theoretical plates may depend on the component to be separated, and may include up to 50 plates, e.g., from 5 to 50, or from 7 to 35, in each column.

Guard Bed

A low total iodide concentration, e.g., up to 5 wppm, e.g., up to 1 wppm, in the purified acetic acid product allows for removal of iodide using a guard bed. The use of one or more guard beds to remove residual iodide greatly improves the quality of the purified acetic acid product. Carboxylic acid streams, e.g., acetic acid streams, that are contaminated with halides and/or corrosion metals may be contacted with the inventive ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with the ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

The pressure during the contacting step is limited primarily by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is up to 5 wppm, e.g. preferably up to 1 wppm. In one exemplary embodiment, the total iodide concentration of the purified acetic acid product may be from 0.01 wppm to 5 wppm, e.g., from 0.01 wppm to 1 wppm. Concentrations of iodide above 5 wppm may require re-processing the off-spec acetic acid. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than 100 wppb iodides, e.g., less than 90 wppb, less than 50 wppb, or less than 25 wppb. In one embodiment, the purified acetic acid composition comprises less than 100 wppb corrosion metals, e.g., less than 750 wppb, less than 500 wppb, or less than 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Example 1

The reactor, containing approximately 900 ppm by weight of rhodium in the form of a rhodium carbonyl iodide compound and approximately 9 wt. % methyl iodide as well as lithium iodide, water, and methyl acetate, was fed with methanol, carbon monoxide and hydrogen to maintain a hydrogen partial pressure of at least about 0.27 atm (i.e. at least about 4 psi). The water concentration was less than 4 wt. %. The reactor maintained a temperature between about 190° C. and 200° C. and operated at a pressure above 28 atm (i.e. above 400 psig). By means of a level control sensing the liquid level within the reactor, liquid reaction medium was continuously withdrawn and fed to the a single-tray flash vessel operating at approximately 150° C. and approximately 3.2 atm (i.e. 32.3 psig). Carbon monoxide recovered from the reactor vent was spraged into the withdrawn reaction medium prior to entering the flash vessel. About 28% of reaction medium exits the as the vapor product stream and the remaining amount is returned as a liquid to the reactor. The vapor product stream was withdrawn at a temperature of approximately 50° C. The vapor product stream composition was follows: 66.35 wt. % acetic acid, 25.01 wt. % methyl iodide; 5.97 wt. % methyl acetate, 1.53 wt. % water, 0.1 wt. % acetaldehyde, and less than 1 wt. % hydrogen iodide.

The vapor product stream was fed to a light ends column to obtain an overhead and a sidedraw stream. A typical example of the HI concentration in sidedraw stream was determined by titrating a sufficient amount of sidedraw stream sample with 0.01 M lithium acetate solution in 50 ml acetone. A pH electrode was used with Metrohm 716 DMS Titrino to determine the end point at Dynamic Equivalence-point Titration mode. HI concentration in wt. % was calculated based on the consumption of lithium acetate titrant as depicted in following equation.

$$HI\ wt.\ \% = \frac{(ml\ of\ LiOAc)(0.01\ M)(128\ g/mole) \times 100}{(g\ sample)(1000\ ml/L)}$$

A sample sidedraw stream composition having about 1.9 wt. % water was tested using this HI titration method. The HI concentrations varied from 50 wppm to 300 wppm, when there was a recycle of the light liquid phase from the overhead light ends to the reaction system. Thus, maintaining the methyl iodide concentration in the vapor product stream contributed to controlling the HI concentrations in the light ends column.

Example 2

The reaction of Example 1 was repeated except the methyl iodide in the reaction medium was approximately 12 wt. % and the pressure of the flash vessel was slightly lower, approximately 3.1 atm (i.e. 30.8 psig). About 31% of reaction medium exited as the vapor product stream and the remaining amount was returned as a liquid to the reactor. The vapor product stream composition was follows: 61.97 wt. % acetic acid, 30.34 wt. % methyl iodide; 5.05 wt. % methyl acetate, 1.54 wt. % water, 0.09 wt. % acetaldehyde, and less than 1 wt. % hydrogen iodide.

A portion of light liquid phase from the light ends overhead was recycled to the reaction system. The sidedraw stream contained 1.5 wt. % water and less than 25 wppm HI, and the balance comprised acetic acid, methyl acetate and methyl iodide. HI concentrations were too low to measure directly with titration. The presence of other cations in the sidedraw made directly measuring HI difficult. The measure of total inorganic iodide, i.e., total possible maximized HI, was done directly. Other inorganic iodides may include lithium iodide, as well as corrosion metal iodide. Again, maintaining the methyl iodide concentration in the vapor product stream beneficially contributed to controlling the HI concentration in the light ends column and ultimately in the sidedraw stream.

What is claimed is:

1. A process for producing acetic acid by carbonylating a methanol reactant feed stream in a reactor in the presence of water, rhodium catalyst, iodide salt and methyl iodide to form a reaction medium, the process comprising:
   separating the reaction medium in a flash vessel into a liquid recycle stream and a vapor product stream comprising acetic acid, from 24 to less than 36 wt. % methyl iodide, from 0.005 to 1 wt. % acetaldehyde, and up to 1 wt. % hydrogen iodide;
   distilling at least a portion of the vapor product stream in a first column to obtain a sidedraw comprising acetic acid; and
   distilling the acetic acid product stream in a second column to recover a stream near the bottom comprising acetic acid.

2. The process of claim 1, wherein the liquid catalyst recycle comprises rhodium catalyst in an amount from 0.01 to 0.5 wt. %, lithium iodide in an amount from 5 to 20 wt. %, corrosion metals in an amount from 10 to 2500 wppm, acetic acid in an amount from 60 to 90 wt. %, methyl iodide in an amount from 0.5 to 5 wt. %, methyl acetate in an amount from 0.1 to 5 wt. %, water in an amount from 0.1 to 8 wt. %.

3. The process of claim 2, wherein the corrosion metals include one or more of iron, nickel, chromium, or molybdenum.

4. The process of claim 1, wherein the sidedraw comprises hydrogen iodide in an amount of less than or equal to 300 wppm.

5. The process of claim 1, wherein the sidedraw comprises methyl acetate in an amount from 0.1 to 6 wt. %.

6. The process of claim 1, wherein the sidedraw comprises methyl iodide in an amount from 0.1 to 6 wt. %.

7. The process of claim 1, wherein the sidedraw comprises methyl iodide in an amount from 1 to 9 wt. %.

8. The process of claim 1, wherein the second column yields an overhead stream comprising water in an amount from 50 to 75 wt. %.

9. The process of claim 1, wherein the stream near the bottom comprises acetic acid in an amount of more than 90 wt. %.

* * * * *